United States Patent [19]
Engelson

[11] Patent Number: 6,024,754
[45] Date of Patent: *Feb. 15, 2000

[54] ANEURYSM CLOSURE METHOD

[75] Inventor: Erik T. Engelson, Menlo Park, Calif.

[73] Assignee: Target Therapeutics Inc., Fremont, Calif.

[*] Notice: This patent is subject to a terminal disclaimer.

[21] Appl. No.: 08/943,039

[22] Filed: Oct. 2, 1997

Related U.S. Application Data

[63] Continuation of application No. 08/588,195, Jan. 18, 1996, Pat. No. 5,749,894.

[51] Int. Cl.[7] .................................................. A61B 17/00
[52] U.S. Cl. ......................... 606/213; 606/191; 606/194; 128/898
[58] Field of Search .................................... 606/213, 214, 606/151, 108, 191, 194, 198, 200; 623/1, 11, 12; 604/49, 52, 53; 128/898

[56] References Cited

U.S. PATENT DOCUMENTS

| | | |
|---|---|---|
| 4,638,803 | 1/1987 | Rand . |
| 4,901,738 | 2/1990 | Brink et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,226,911 | 7/1993 | Chee et al. . |
| 5,342,394 | 8/1994 | Matsuno et al. . |
| 5,429,635 | 7/1995 | Purcell, Jr. et al. . |
| 5,449,354 | 9/1995 | Konwitz et al. . |
| 5,454,794 | 10/1995 | Narciso et al. . |
| 5,454,807 | 10/1995 | Lennox et al. . |
| 5,522,836 | 6/1996 | Palermo . |

FOREIGN PATENT DOCUMENTS

WO 94/24962  11/1994  WIPO .

*Primary Examiner*—Michael Buiz
*Assistant Examiner*—Tina T. D. Pham
*Attorney, Agent, or Firm*—Morrison & Foerster LLP

[57] ABSTRACT

This is a procedure for stabilizing or filling an aneurysm in the vasculature. The procedure involves the introduction into the aneurysm of a solid vaso-occlusive device such as a coil or braid and a polymeric composition which may be reformed or solidified in situ. The solid vaso-occlusive device is at least partially surrounded or enveloped by that polymeric composition. The polymeric composition is reformed via light, heat, R.F. or the like to form a rigid mass with the solid vaso-occlusive device. These steps may be carried out sequentially or the steps of introducing the vaso-occlusive device and reforming the polymeric composition may be carried out simultaneously. The procedure may be accomplished using intravascular catheters to access the desired site and to deliver the noted materials.

8 Claims, 9 Drawing Sheets

ANEURYSM CLOSURE METHOD

This application is a continuation of application Ser. No. 08/588,195, filed Jan. 18, 1996 now U.S. Pat. No. 5,749,894.

FIELD OF THE INVENTION

This invention is a procedure for stabilizing or filling an aneurysm in the vasculature. The procedure involves the introduction into the aneurysm of a solid vaso-occlusive device such as a coil or braid and a polymeric composition which may be reformed or solidified in situ. The solid vaso-occlusive device is at least partially surrounded or enveloped by that polymeric composition. The polymeric composition is reformed via light, heat, R.F. or the like to form a rigid mass with the solid vaso-occlusive device. These steps may be carried out sequentially or the steps of introducing the vaso-occlusive device and reforming the polymeric composition may be carried out simultaneously. The procedure may be accomplished using intravascular catheters to access the desired site and to deliver the noted materials.

BACKGROUND OF THE INVENTION

Endovascular therapy has long been used in treating a variety of different conditions, including control of internal bleeding, occlusion of blood supply to tumors, and relief of vessel wall pressure in the region of an aneurysm. A variety of different embolic agents are known as arguably suitable for such therapy.

One such class of embolic agents includes injectable fluids or suspensions, such as microfibrillar collagen, various polymeric beads, and polyvinyl alcohol foam. The polymeric agents may be additionally crosslinked, sometimes in vivo, to extend the persistence of the agent at the desired vascular site. These agents are often introduced into the vasculature through a catheter. After such introduction, materials there form a solid space-filling mass. Although they provide good short-term vaso-occlusion, they are ultimately reabsorbed in the process of vessel recanalization.

Polymer resins, typically cyanoacrylates, are also employed as injectable vaso-occlusive materials. The resins are typically mixed with a radio-opaque contrast material or made radiopaque by the addition of tantalum powder. Their use is fraught with problems in that placement of the mixture is quite difficult. Inadvertent embolisms in normal vasculature (due to the inability of controlling the destination of the pre-gelled resins) is not uncommon. The material is also difficult or impossible to retrieve once it has been placed in the vasculature. Such resins have not been FDA approved, a waiver must be requested in each instance where the materials are applied during human operative procedures.

Other materials said to be suitable for use in forming occlusions in the body are discussed in WO 94/24962, published Nov. 10, 1994, to Pathak et al. The materials discussed there are generically polymers which may be heated to a molding temperature in the human body by application of light. Typical of such materials are crystalline or semi-crystalline polymers which will undergo a transition to a cohesive but viscous fluid when subjected to heating. Preferable are bioerodible polymers continuing chromophores which absorb light in the region of the electromagnetic spectrum chosen, e.g., polycaprolactone homopolymers with an indocyanine green or copper phthalocyanine dye compounded therein. The preferred method of using these compositions is for the supply of drugs or other therapeutic agents.

More common are mechanical vaso-occlusive devices. One such device is a balloon which may be carried to the vessel site at the end of the catheter and there inflated with a suitable fluid, typically a polymerizable resin, and released from the end of the catheter. The balloon device has the advantage that it effectively fills the cross-section of the occluded vessel. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter. Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

Another type of mechanical vaso-occlusive device is a wire coil or braid which can be introduced through a catheter in stretched linear form and assumes an irregular shape upon discharge of the device from the end of the catheter. A variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils used previously, Ritchart et al. teaches a coil which is fairly soft and is delivered to the site using a pusher within a catheter lumen. The Ritchart et al. coils are typically pushed into the desired vascular site in a linear configuration. Upon discharge from the delivery catheter, the coil may undertake any of a number of random or regular configurations designed to fill the site. The coils are used for small vessel sites, e.g., 0.5–6 mm in diameter. The coils themselves are said to be between 0.010 and 0.030 inches in diameter. The length of the coiled wire is typically 15–20 times the diameter of the vessel to be occluded. The wire used to make up the coils may be 0.002 to 0.006 inches in diameter. Tungsten, platinum, and gold threads or wires are said to be preferred. These coils have a variety of benefits, including the fact that they are relatively permanent, they can be easily imaged radiographically, they may be located at a well-defined vessel site, and they can be retrieved.

A variation of the mechanical endovascular coil is the electrolytically detached endovascular coil described in U.S. Pat. No. 5,122,132, to Guglielmi et al. Guglielmi's coils are typically used in intracranial aneurysms because of their effectiveness in quickly forming controlled emboli. The disclosed coils are similar to those of Ritchart et al. in size and in composition. However, the method of placing the coil to the vascular site is radically different. Rather than mechanically thrusting the coil into the chosen site, the coil is placed at the site and a small voltage is applied to the corewire supporting the coil so that the coil is electrolytically detached from the distal tip of the guidewire. The step of electrolytically detaching the coil may have the added benefit of forming a thrombus as the coil is detached. Again, as noted above, the Guglielmi coils may be stainless steel or platinum or the like, and are typically 0.010 to 0.020 inches in diameter and are made using wire having approximate diameters of 0.001 to 0.005 inches. The coils in this service are typically between 1 and 50 centimeters in length.

None of these references teach the concept of filling an aneurysm with a mechanical occluding device and holding it there by the use of a reformable polymer.

SUMMARY OF THE INVENTION

This invention is a medical procedure for stabilizing and filling vascular aneurysms. The procedure involves the steps of sequentially or simultaneously at least partially filling the selected aneurysm with a mechanical vaso-occlusive device such as a coil or a braid and further with a formable polymeric composition. The vaso-occlusive device may be at least partially coated with the formable polymeric composition. The polymeric composition infills the interstices of the mechanical vaso-occlusive device upon treatment with light or radio frequency radiation.

The mechanical vaso-occlusive devices used in this invention may be any of a wide variety of devices known in the art. The mechanical vaso-occlusive device may be introduced through a vascular catheter. Various coils or braids may be mechanically attached to the pusher; they may be physically pushed, electrolytically detached from a pusher joined to the pusher or core wire; they may be joined to the pusher using mechanical joints. In some instances, the mechanical vaso-occlusive device may be delivered using a fluid stream such as saline. It is desirable to partially fill the aneurysm with the mechanical device to form a mechanical framework for the polymeric composition. Preliminarily, it may be desirable to coat the mechanical vaso-occlusive device with the polymeric composition. The mechanical vaso-occlusive device may be used in conjunction with fibrous adjuncts, e.g., tufts or braided coverings or the like, to enhance the thrombogenicity.

The following or concurrent step involves introduction of a polymeric material which can be coalesced, reformed, or solidified in the vasculature by use of heat applied with an amount of radiant energy, e.g., R.F. or light. The polymeric material reforms about the mechanical vaso-occlusive device upon the application of heat or, if particulate, coalesces to the interior form of the aneurysm.

DESCRIPTION OF THE INVENTION

Figure 1:
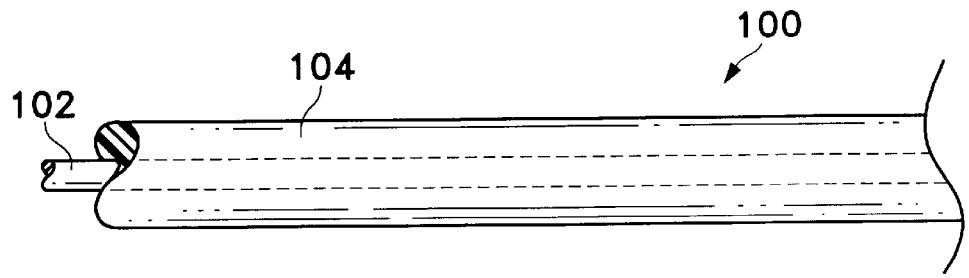
FIG. 1 shows in a partial cross-section a wire using a vaso-occlusive device coated with a formable polymer.

As has been noted above, this invention is a medical procedure for stabilizing and at least partially filling vascular aneurysms. The procedure involves the steps of sequentially or simultaneously filling the selected aneurysm both with a mechanical vaso-occlusive device and with a formable polymeric composition. Upon application of light or radio frequency radiation to the polymeric composition, the polymeric composition is physically reformed to infill at least a portion of the mechanical vaso-occlusive device and thereby at least partially fill the aneurysm.

Formable Polymers

The polymeric materials used in this invention desirably have two physical parameters which are desirable when using light to cause the reformation in the body. Those two physical parameters are first that the material be substantially crystalline or semi-crystalline so that when heated to its glass or melting temperature, it undergoes a transition to a viscous fluid that flows readily and yet remains cohesive. The other desirable physical parameter is that the polymeric material be able to absorb light energy from the light source in a spectrum that is not readily absorbed by the surrounding body tissue. When the inventive procedure is used in conjunction with an RF source to load energy into a metallic vaso-occlusive device, obviously it is not necessary that the polymeric material be able to absorb light.

In either variation of the invention, the polymeric material must be moldable or reformable at a temperature that does not cause substantial harm to the tissue in the aneurysm nor the surrounding blood. The polymeric material must be reformable at a temperature above that found in the body. That is to say that the body should not be able to reform the polymer by a fever or the like. Such temperature is 104–106° F. Such a temperature relates in general to either a melting temperature $T_m$ or a glass transition temperature $T_g$ at which the polymeric composition may be reformed. Polymeric compositions are always mixtures of different molecular weights and configurations and consequently melt or undergo a glass transition over a temperature range. Nevertheless, the engineering cience related to polymeric compositions provides several well defined pathways for defining such temperatures. In a functional sense, however, the polymeric composition itself must simply be formable and able to coalesce or remain in a coherent mass at a temperature above that found in the human body and below that temperature where harm is caused to the surrounding tissues and fluids.

The polymeric composition must obviously be biocompatible. Furthermore, since it is to remain in the human body as the glue or a means for making the vaso-occlusive device self-adherent, it should not be substantially bioerodible.

The polymeric material should be substantially crystalline or have a semi-crystalline structure or have a component of such a material. It is desirable that the viscosity of the material be such that it has a modest amount of flowability at the chosen reformed temperature. The viscosity of the polymeric material at the reformed temperature should be such that it will self-coalesce without substantial outside forcing. The surface tension of the moldable polymeric composition should also be measured for suitability prior to an initial use.

Suitable polymeric materials include such polymers as polyalkenes (polyethylene, polypropylene, and polybutene), polymethacrylates, polyacrylates, polyesters, polyamides (particularly the Nylons) and polysaccharides. Co-polymers, blends, alloys, block copolymers of the noted materials are also suitable. Bimodal compositions of a crystalline polyethylene or polypropylene may be produced using the cyclopentadiene catalysts described by a number of patents owned either by Exxon Chemical Patents, Inc. or BASF. Narrow molecular weight distribution Nylons are also available. Multi-modal atomic weight distributions are particularly suitable because of their ability to be gradually melted while maintaining a component which does not undergo a transition. In this way, the higher molecular weight material provides, in concept, a background or skeleton maintaining the coherence of the polymeric mass during the reformation step. The overall molecular weight of the material is nevertheless maintained at a level such that it is neither absorbed into physiological fluids or tissue.

When used in the procedure described below where a light source is used as the energy source for reformation of the polymeric composition, the overall polymeric composition must be able to absorb the light in an amount sufficient to cause the reforming or phase change into a flowable composition. In some instances, e.g., where the size of the crystalline subphases of a bimodal polymeric composition are of a size that is suitable for absorption of particular wavelengths, or the color of the material is such that it absorbs light in a particularly suitable wavelength range, it is not necessary to add dyes, pigments, or other chromophores. However, in most biologically suitable polymeric compositions, a dye or pigment is necessary. Suitable lasers and appropriate dyes are known. For instance, the following is a list of lasers and dyes which may be matched to provide a polymeric composition with an appropriate color for introduction of energy by nominated laser.

| Laser (wavelength-nm) | Dye (absorption-nm) |
| --- | --- |
| Argon ion (457 nm) | Acramine Yellow (420 nm) |
| Argon ion (488 nm) | Acridine Orange (489 nm) |
|  | Fluorescein (491 nm) |
| Argon ion (514 nm) | Eosin Y (514 nm) |
| Argon/Krypton (676 nm) | Methylene Blue (661 nm) |
| Krypton (647 nm)/Krypton (676 nm) | Jenner stain (651 nm) |
|  | Methylene Blue (661 nm) |
| Ruby (694 nm) | Prussian Blue (694 nm) |
| Neodymium: YAG (frequency doubled, 532 nm) | Ethyleosin (532 nm) |
|  | Erythrosin B (525 nm) |
|  | Eosin Y (514 nm) |
| Neodymium: YAG (frequency doubled, 355 nm) | Acridine (358 nm) |
| All | Carbon Black |

Obviously, the selection of light source and chromophore is not intended to be limited to those noted just above. Other selections of light source and chromophore are suitable for this invention.

Introduction of the chromophore into the polymeric composition is a procedure well known in the polymer engineering art. Solid dyes or pigments may be physically compounded into the material perhaps with the application of heat. The liquid dyes may be chemically bound to the polymer or may be simply mixed with the material if such is appropriate.

The use of chromophores and dyes is for the specific purpose of limiting the absorption of light, and hence temperature increase, to the polymeric composition and in minimizing the amount of heat applied to the surrounding tissues and fluids. Consequently, selection of an appropriate dye and composition is therefore to be undertaken with an eye towards the absorptive characteristics of the surrounding tissue.

Vaso-occlusive Devices

A variety of vaso-occlusive devices are suitable for use in combination with the polymeric composition described above in carrying out the procedure of this invention. In particular, a number of specifically suitable vaso-occlusive devices are already known which are particularly useful for the practice of this invention. As will be discussed below, it is highly desirable that these vaso-occlusive devices be coated or otherwise associated with the polymeric compositions described above so that a modest application of light or radio frequency energy is able to cause various sections of the vaso-occlusive device to adhere one section to the other.

FIG. 1 shows the most basic of the vaso-occlusive devices suitable for use in this invention. In particular, it is a coated wire (100) comprising an inner metallic core (102) at least partially coated by an outer polymeric coating (104) of the polymeric compositions described above. The wire core is preferably of a biocompatible material such as one or more members of the Platinum Group, i.e., platinum, palladium, rhodium, rhenium, etc.; tungsten, any of a variety of stainless steels known and accepted for use in the human body; and gold. Especially preferred are alloys, particularly alloys of platinum and tungsten. Known methods of placing such polymeric materials on the exterior of core wires (102) will be certainly acceptable.

Figure 2:
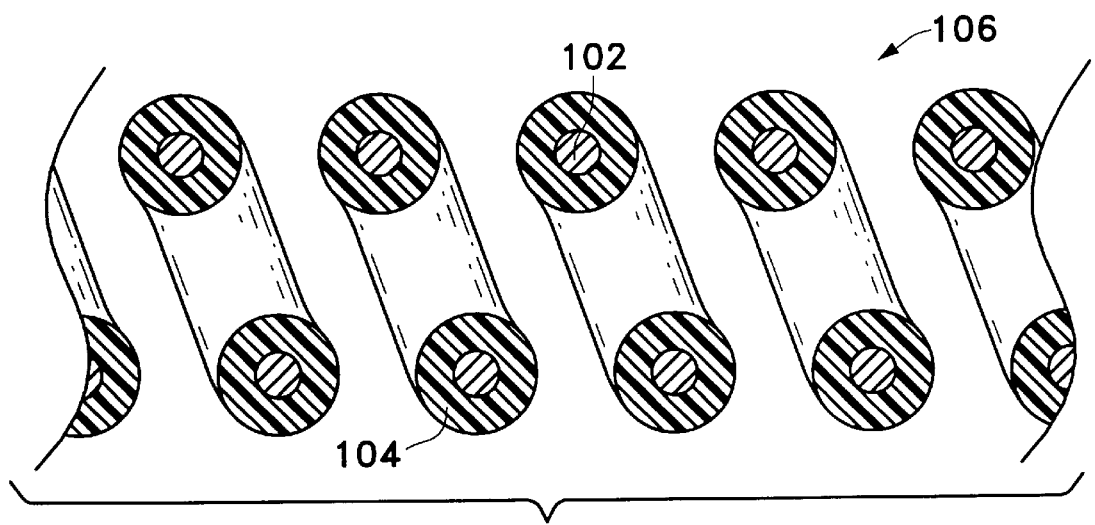
FIG. 2 shows in cross-section a helical coil made of the device shown in FIG. 1.

FIG. 2 shows in cross-section a helically wound coil comprising a wire (102) and a polymeric coating (104). This configuration is known as a "primary winding". A variety of vaso-occlusive devices made up of only primary winding as well as secondary windings such as that shown in FIG. 3 are sold by Target Therapeutics, Inc. of Fremont, Calif.

Figure 3:
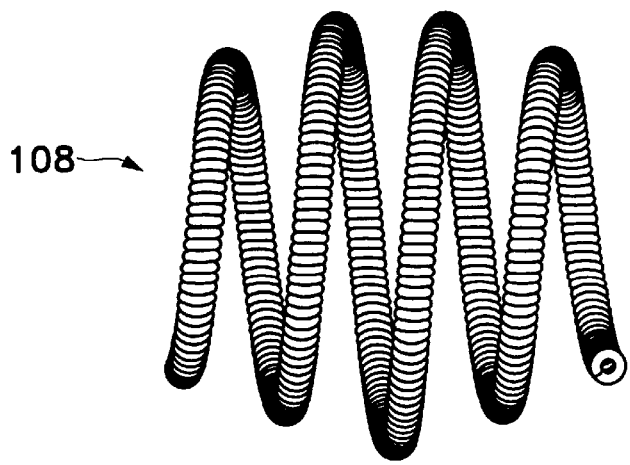
FIG. 3 shows a coil design having a secondary shape made of the FIG. 2 device.
Figure 4:
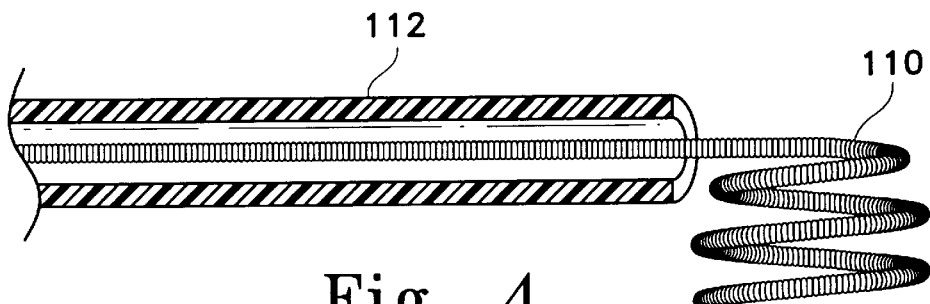
FIG. 4 shows a simple helical coil having fibers wrapped therethrough.

FIG. 3 shows a vaso-occlusive device (108) having a "secondary winding" which in turn is made up of the primary wound coil (106) shown in FIG. 2. A variety of devices having secondary forms are known in the prior and are conversely available. The first of such devices is described in the Ritchart et al. patent noted above. The concept of the use of such secondary shapes is shown in FIG. 4. This concept is described further in the Ritchart et al. patent. Nevertheless, FIG. 4 shows the ejection of a coil (110) having a secondary shape from the distal tip of delivery catheter (112). The delivery catheter maintains the coil in a generally linear condition prior to the time that it is ejected from the catheter. As the coil (110) emanates from the distal end of the catheter (112), it assumes a shape which has been previously placed on the coil during its construction. As will be described later, the secondary shape of coil (110) is desirable to fill an aneurysm or other physiological site.

Figure 5:
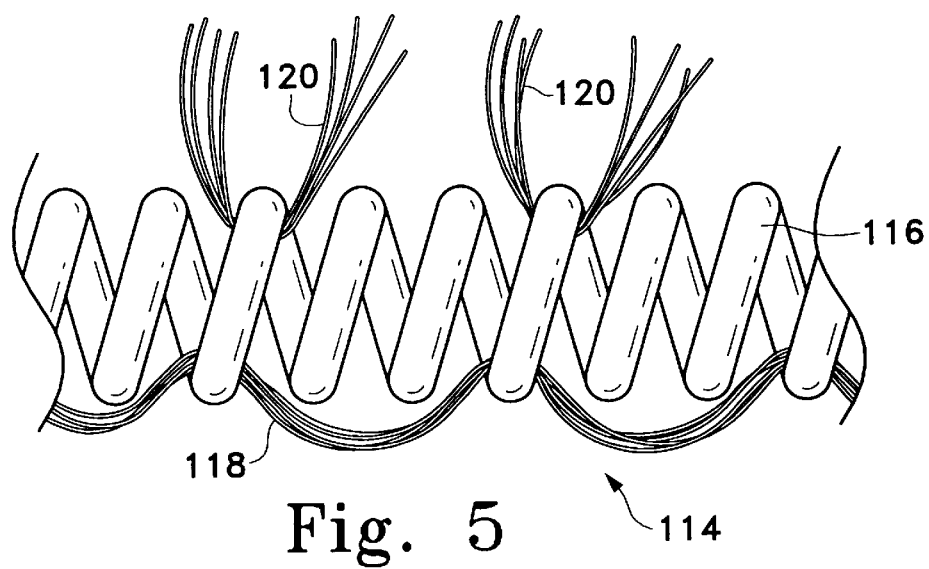
FIG. 5 shows a partially ejected coil having a secondary shape. The catheter is in cross-section.

FIG. 5 shows a variation of a vaso-occlusive coil assembly in which the central helically wound coil (116) is provided with a variety of fibrous adjuncts. In particular, the fibers may be looped through the turns of the coil such as fibers (118) or may be placed as tufts (120). The fibers may be any of a wide variety of materials known to those in this art. Particularly desirable are materials such as polyesters (Dacron), cotton, and silk. Structures such as are shown in FIG. 5 are described in Chee et al. (U.S. Pat. No. 5,226,911).

Figure 6:
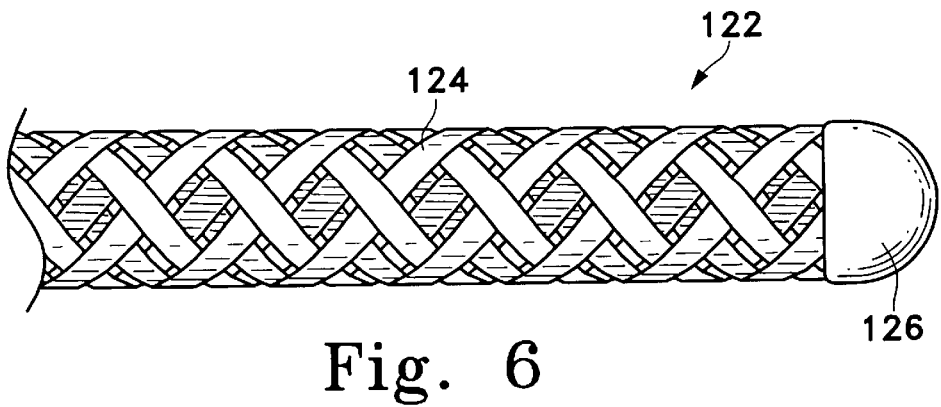
FIG. 6 shows a braided vaso-occlusive device.

In addition to the helically wound vaso-occlusive coils described above, another variation of a vaso-occlusive device is shown in FIG. 6. In this variation, a vaso-occlusive braid (122) is seen. The material making up the strands (124) of braided device (122) typically are metallic, e.g., the same material as used in producing the helical coils described in the figures just above. It is also within the scope of this invention that at least a portion of the fibrillar components making up braid (122) are polymeric in nature. The cross-sections of the braid components may be ribbon-like or may be of circular cross-section. As is the case with the termination of the helical coils described above, a termination piece (126) terminates the device (122). These termination pieces (126) may be made by simply heating the end of the braid or coil so to melt the material that is found in the device or an ancillary material, e.g., an epoxy or thermoplastic may be simply applied to the end of the braid or coil in a molten or liquid form. Fibers may be added to the braided vaso-occlusive device as needed or desired to increase the overall thrombogenicity of the device.

There are a variety of ways to deliver the vaso-occlusive devices described above to a selected site within the human body. Currently the most common and likely the most widely used is simply the use of a pushed vaso-occlusive device.

Figure 7:
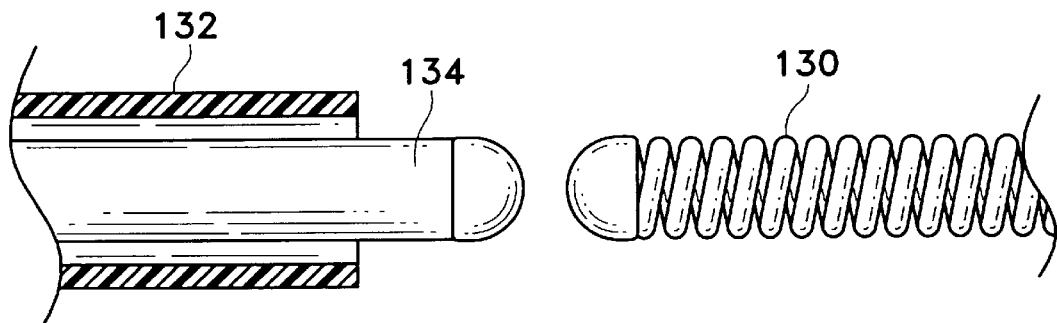
FIG. 7 shows in partial cross-section a vaso-occlusive device being ejected from a catheter by use of a pusher.

FIG. 7 shows a pushed device (130). Although device (130) is shown as a vaso- occlusive coil, it may be a braid or may entail secondary forming, as is discussed above with relation to FIG. 3. It is a simple arrangement in which pushed vaso-occlusive device (130) ejected from the tip of catheter (132) using a pusher (134). The pusher may be an elongated, wire-liked device specially fabricated for such a service. Alternatively it may be a guidewire or the like pressed into secondary service for this purpose. The description of such a procedure is found in the patent to Ritchart et al.

Figure 8:
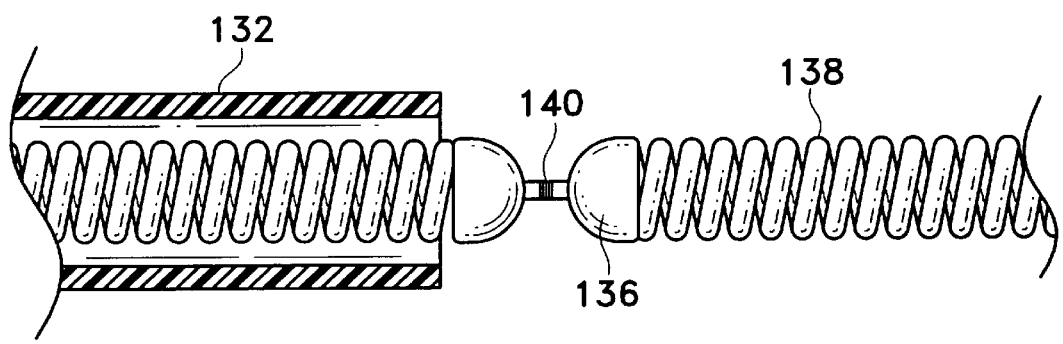
FIG. 8 shows a pusher joined to a vaso-occlusive device having an electrolytically severable joint between the pusher and the vaso-occlusive device.

An alternative device is shown in FIG. 8. As was described above in discussing the Guglielmi et al. patent, vaso-occlusive devices may be more precisely placed using an electrolytically severable joint between the pusher and the vaso-occlusive device. FIG. 7 shows such an arrangement. The delivery catheter (132) contains a pusher (136), a vaso-occlusive device (138), and an electrolytically severable joint (140) between pusher (132) and vaso-occlusive device (138). Generally, the electrolytically severable joint (140) is constructed of material which is most base in the electromotive series of the various components of the system shown in FIG. 8. A voltage is applied to pusher (136), and it flows through the joint (140) and partially through coil (138). The voltage returns to the power supply, providing current to pusher (136) via another path not shown in FIG. 8. Nevertheless, the voltage passing to electrolytically severable joint (140) provides a source of erosion or oxidation or electrolysis which tends to erode that electrolytic joint (140). The arrangement depicted in FIG. 8 permits an attending physician using the system to precisely place the vaso-occlusive device at a selected physiological site. One problem which had occurred on occasion using the pusher-actuated coil, as shown in FIG. 7, is that the ejection of the coil causes the catheter to rebound upon completion of the delivery. In some instances, the coil was not as properly placed as it might have been. Consequently, the attending physician would then find it necessary to reposition the coil or remove it completely for placement of an additional coil.

The Guglielmi detachable coil (GDC) is more desirable from a placement standpoint in that the physician can place the coil accurately in its final position within the selected site prior to releasing it from the pusher by use of electrolysis.

Figure 9:
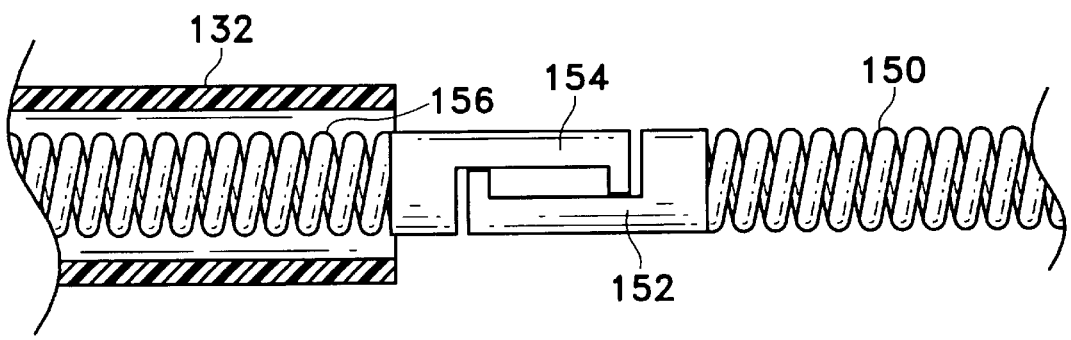
FIG. 9 shows in partial cross-section a mechanical joint between a vaso-occlusive device and a pusher.

Another generic group of devices which allow fairly precise placement of the embolic device is generally shown in FIG. 9. In FIG. 9 the embolic coil or other device (150) has a mechanical clasp (152) which mates with another mechanical clasp (154) found on the end of pusher device (156). Again, the necessary delivery catheter (132) is also shown. A variety of mechanical joints are known, and many of them are described in patents owned Target Therapeutics, Inc. of Fremont, Calif.

It is within the scope of this invention that each of these devices, as described above, may be used either partially coated with a polymeric composition, as further described above, or may be introduced before or after the introduction of the polymeric composition by itself. It is desirable that the vaso-occlusive devices be coated because it is then less likely that the polymers will migrate from the selected site. Furthermore, they are in intimate connection with the devices themselves and so are able to cause the various sections of the devices to adhere to each other.

Procedures

The various procedures according to the invention here are described with respect to the figures discussed below.

Figure 10A:
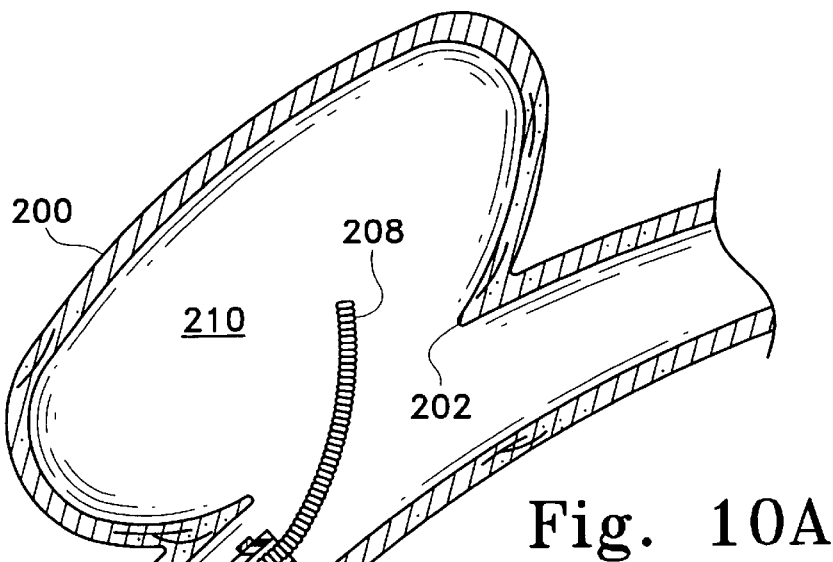
FIGS. 10A, 10B, 10C, and 10D show steps of introducing a vaso-occlusive device and a formable polymer into an aneurysm.

FIG. 10A shows the first step of what likely is an initial step in any procedure used in practicing the invention described herein. FIG. 10A shows an aneurysm (200) having a neck (202). A delivery catheter (204) typically having one or more radiopaque markers (206) at its distal tip is shown approaching the neck, of the aneurysm. A guidewire (208) is shown entering aneurysm space (210). Subsequent to the step shown in FIG. 10A, the catheter body itself will follow or be guided by guidewire (208) so that the distal tip of catheter (204) is within the aneurysm space (210). The guidewire will then be withdrawn to allow introduction of other vaso-occlusive material according to the invention.

Figure 10B:
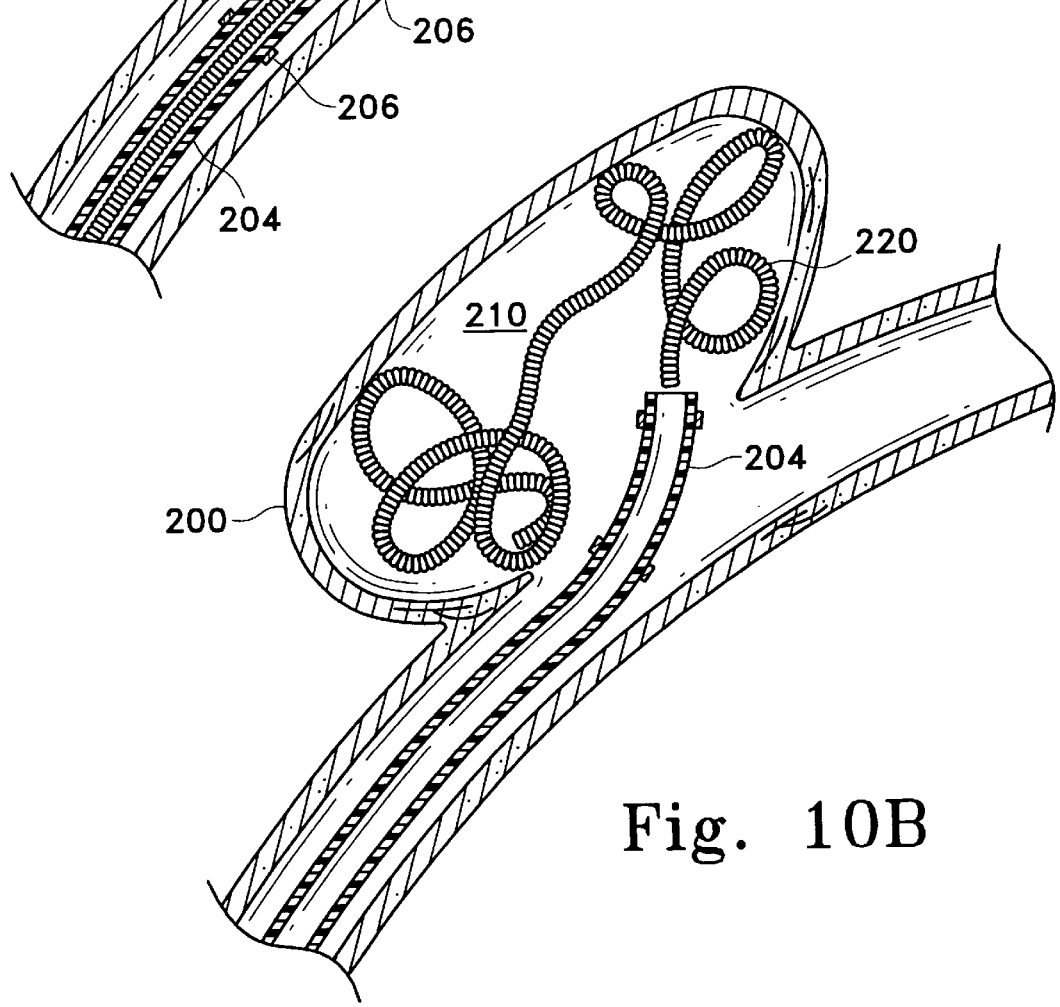

FIG. 10B shows a following step in which a vaso-occlusive device (220) is ejected from the distal tip of catheter (204). In this instance, the vaso-occlusive device (220) is shown to be a coil having secondary form which is generally somewhat random in nature. In this variation of the invention, the coil may be coated with a polymeric composition, although it need not necessarily so done. As may be seen from FIG. 2B, the coil (220) generally fills space (210) of aneurysm (200).

Figure 10C:
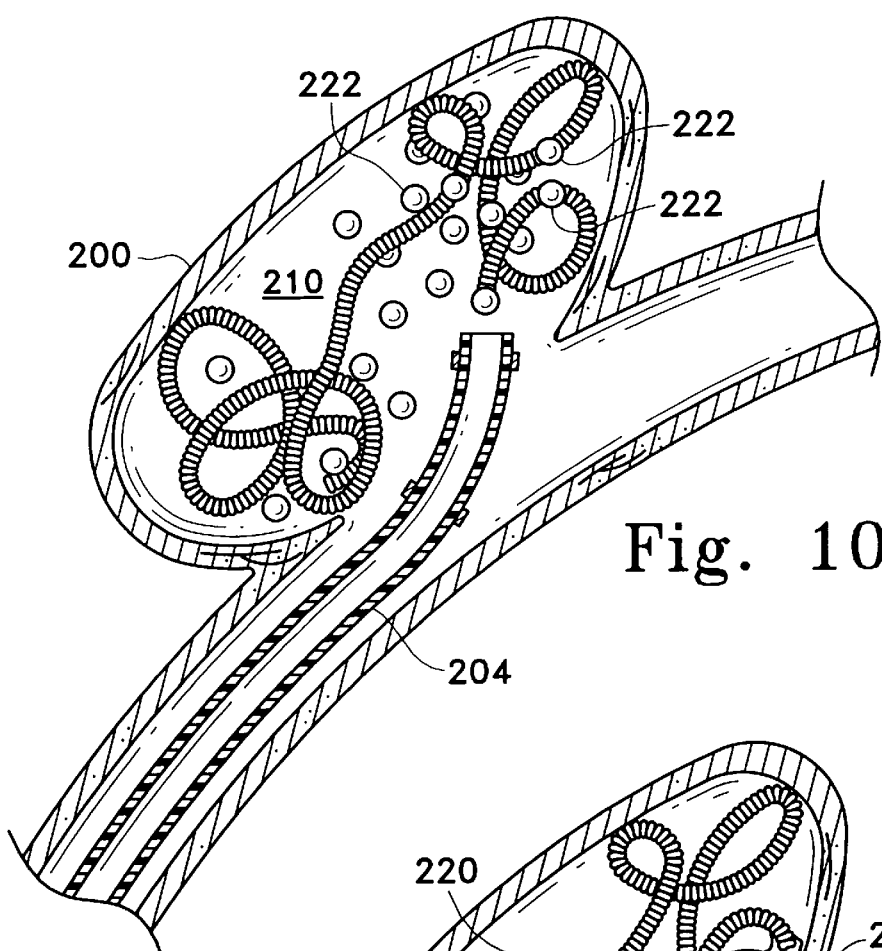

FIG. 10C shows a following step in which modest globules (220) of polymeric composition are introduced into the space (210) inside the aneurysm (200). In this case the material is shown to be in the form of a bead which may be then coalesced into a coherent mass in a following step. These beads (222) may be introduced into the aneurysm in a number of ways, including use of a physical or mechanical pusher to press them into the aneurysm (200) or perhaps with the use of a flowing saline stream. Obviously, care must be taken so that the distal tip of the catheter is not ejected from the aneurysm mouth. Furthermore the catheter tip must be sufficiently far into the aneurysm that the beads (222) not be in a position that they can leave the aneurysm to flow down the bloodstream and into an unwanted region of the body.

Figure 10D:
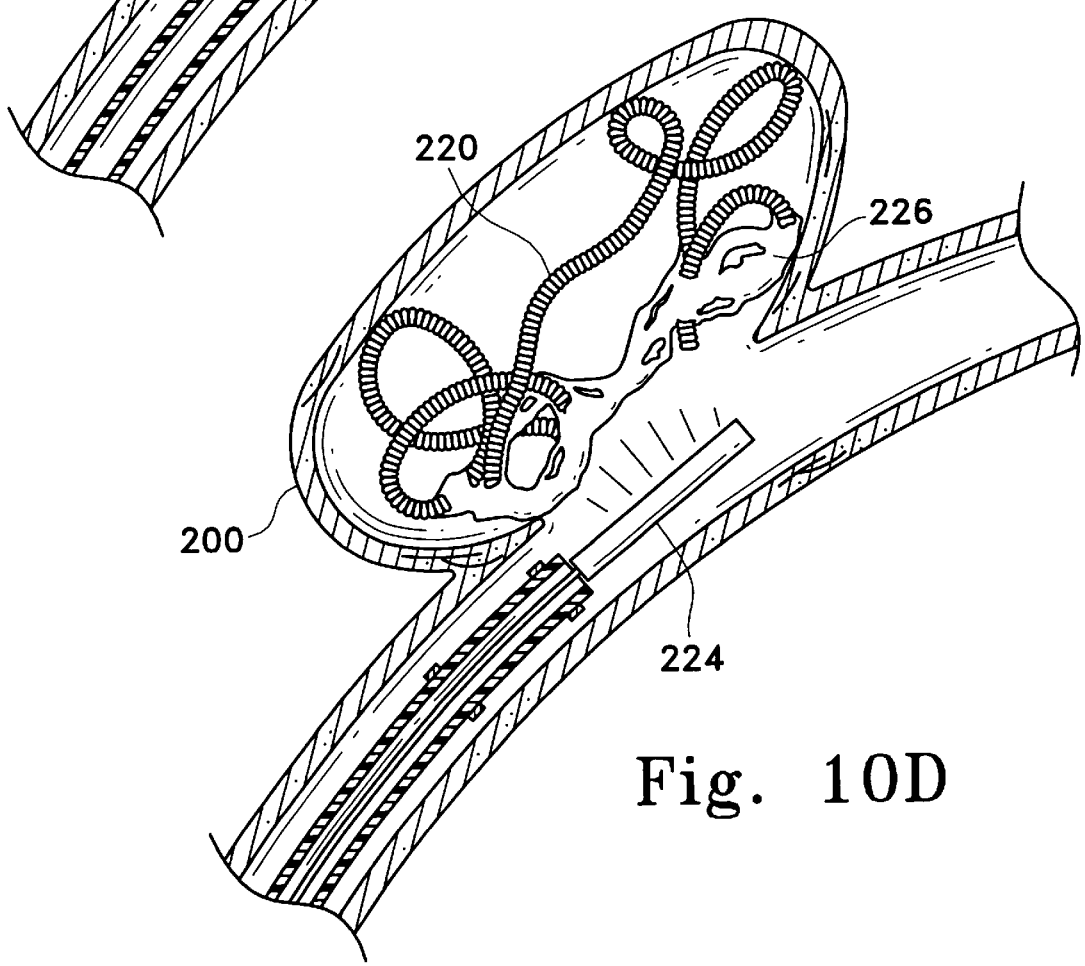

FIG. 10D shows the final step in the procedure in which the delivery catheter has been withdrawn and a light-emitting device (224) has been introduced into the region just outside the mouth of the aneurysm (200). The light source is activated and the mouth of the aneurysm is sealed by the resulting plug (226) because of the reforming of the polymeric composition introduced into the aneurysm as beads, as shown in FIG. 10C and potentially as a coating on the vaso-occlusive device (220). This procedure seals the aneurysm and prevents it from seeing the pulsing pressure found in the artery outside the mouth of aneurysm (200). The procedure outlined in FIGS. 10A–10D may be carried out in an incremental manner. That is to say that a number of beads (222) may be introduced into the aneurysm (200), the polymer cured via the use of the light source (224), other beads (222) included, and subsequent light source (224) treatment step. This alternation may be repeated as desired.

FIGS. 11A, 11B, 11C, and 11D show a minor variation of the procedure found in the FIG. 10 series. In this variation, the aneurysm (200), having inner space (210) is again shown as having guidewire (208) and a trailing catheter (204). It is the same first step as was found in FIG. 10A. The delivery catheter (204) then follows guidewire (208) until the distal tip of catheter (208) is introduced into aneurysm space (210).

Figure 11A:
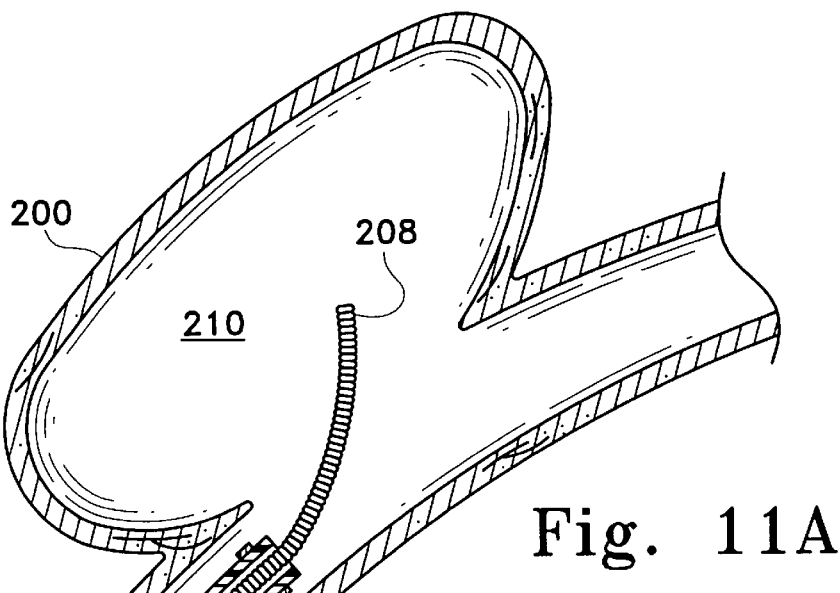
FIGS. 11A, 11B, 11C, and 11D show in the introduction of a vaso-occlusive device and a formable polymer into an aneurysm.
Figure 11B:
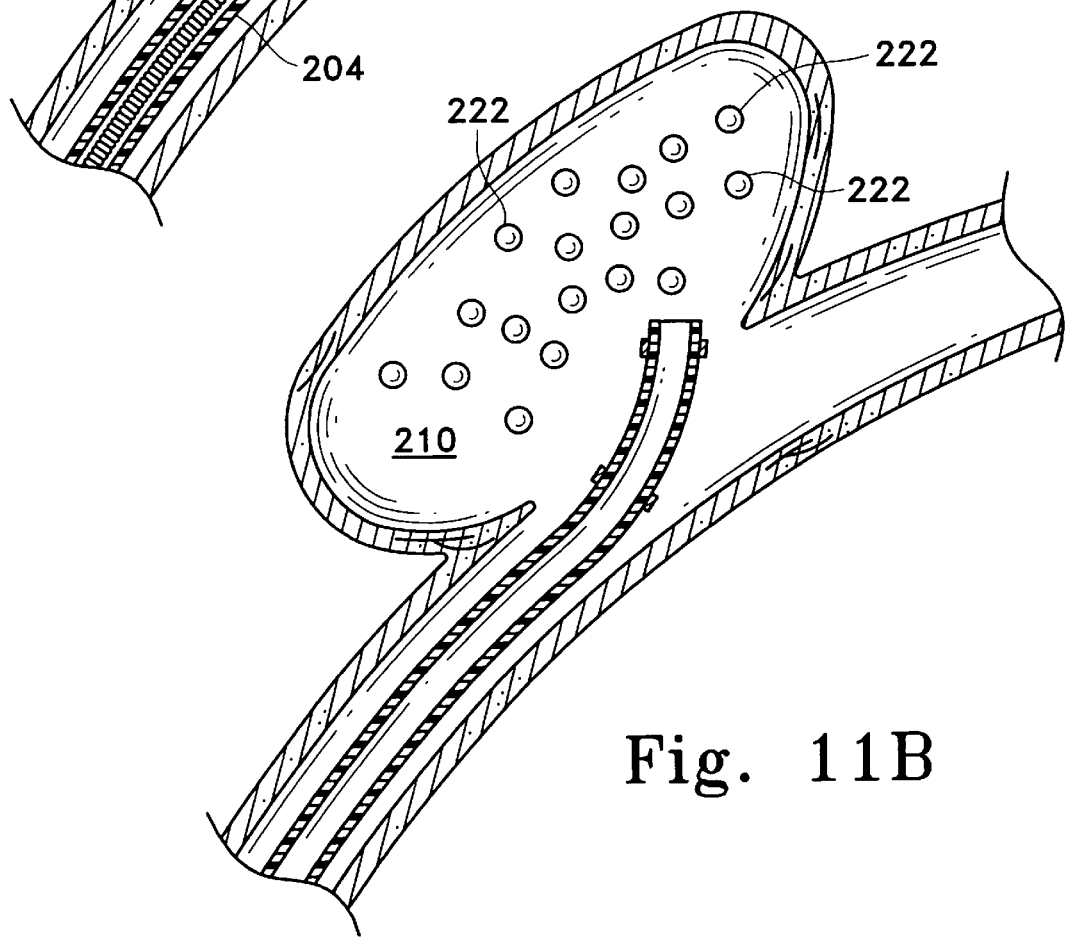

FIG. 11B shows the introduction of a number of polymeric composition globules (222) into the aneurysm space (210).

Figure 11C:
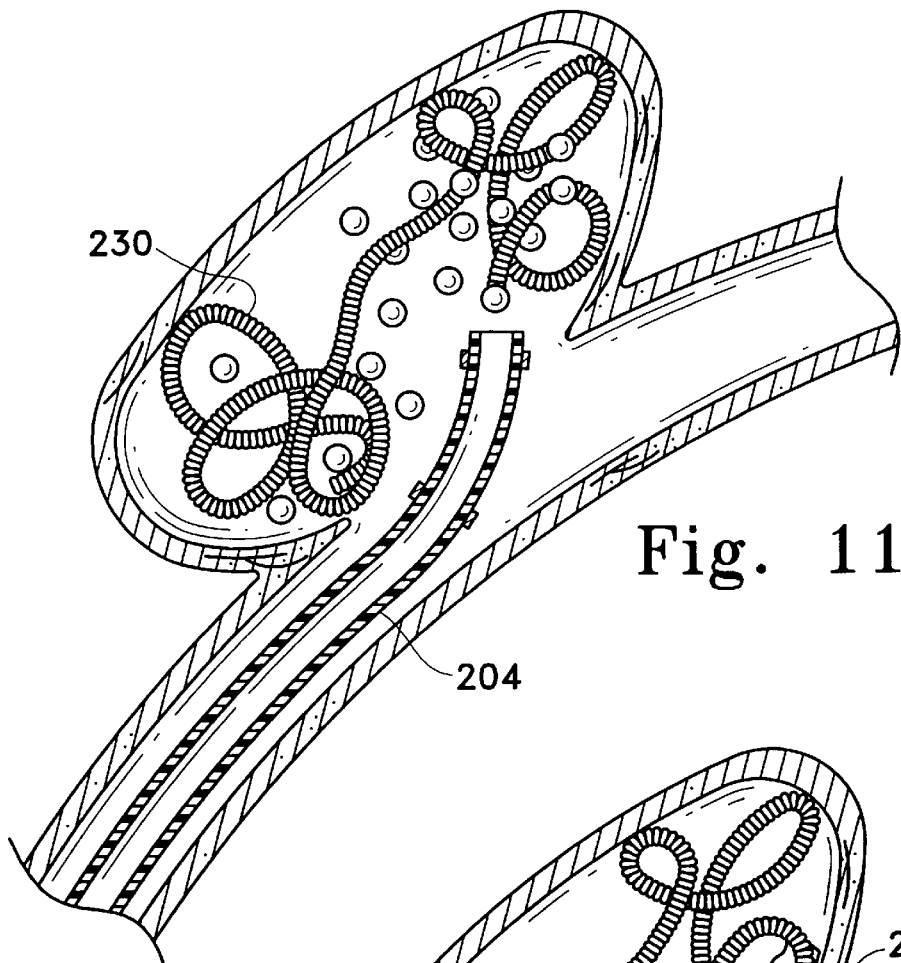
Figure 11D:
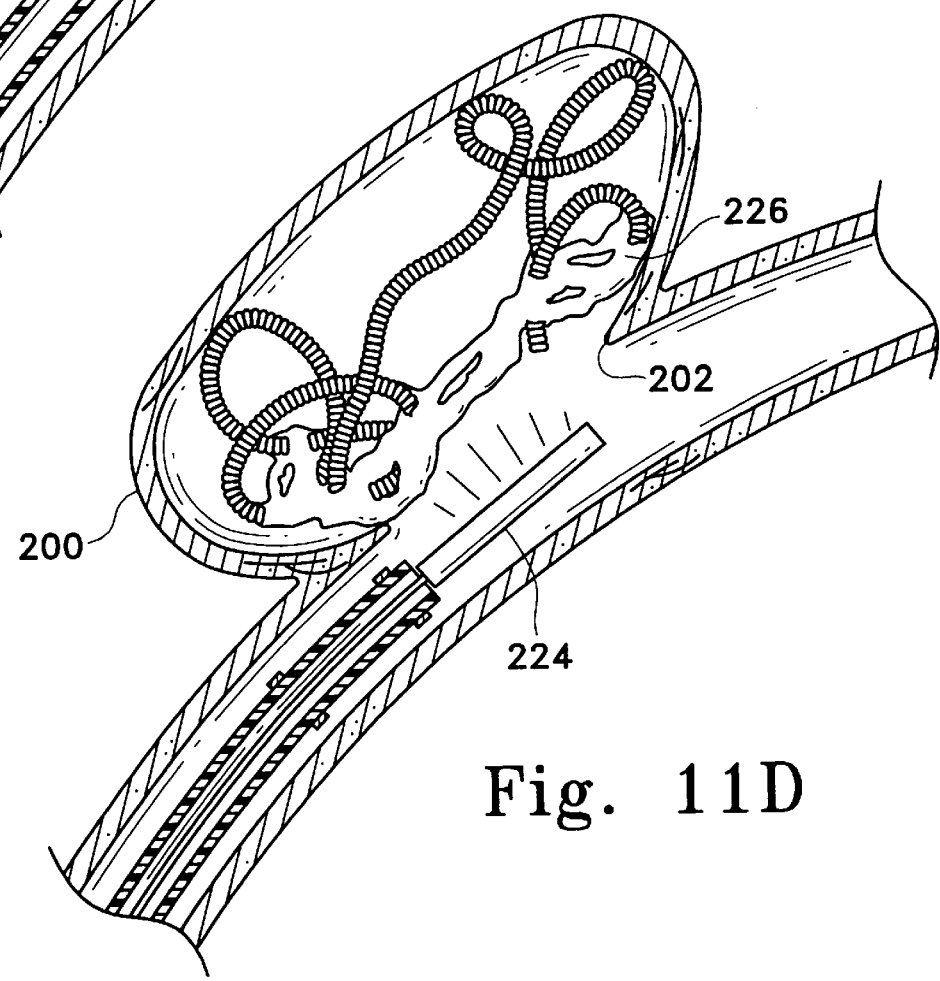

FIG. 11C then shows catheter (204) as introducing a coil-like vaso-occlusive device (230), which is similar to (222) found in FIGS. 10B and 10C.

FIG. 10D again shows the use of a light-emitting (224) to coalesce and solidify the polymeric composition into a plug generally blocking the mouth (202) of the aneurysm (200). This step is the same as that shown in FIG. 10D.

Figures 12A, 12B:
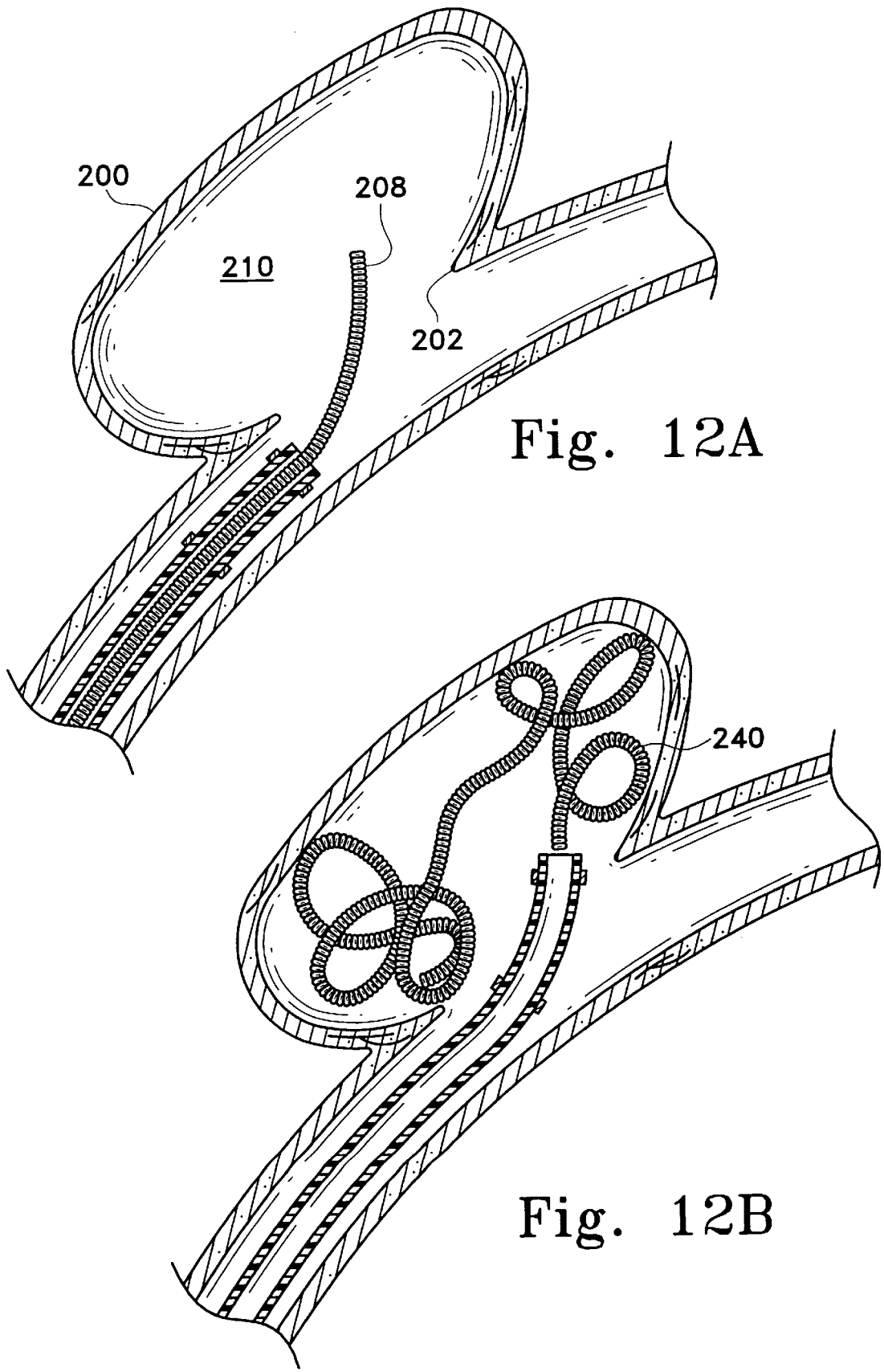
FIGS. 12A, 12B, and 12C show the steps of introducing a vaso-occlusive device which is at least partially coated with a formable polymer into an aneurysm using the process of this invention.
Figure 12C:
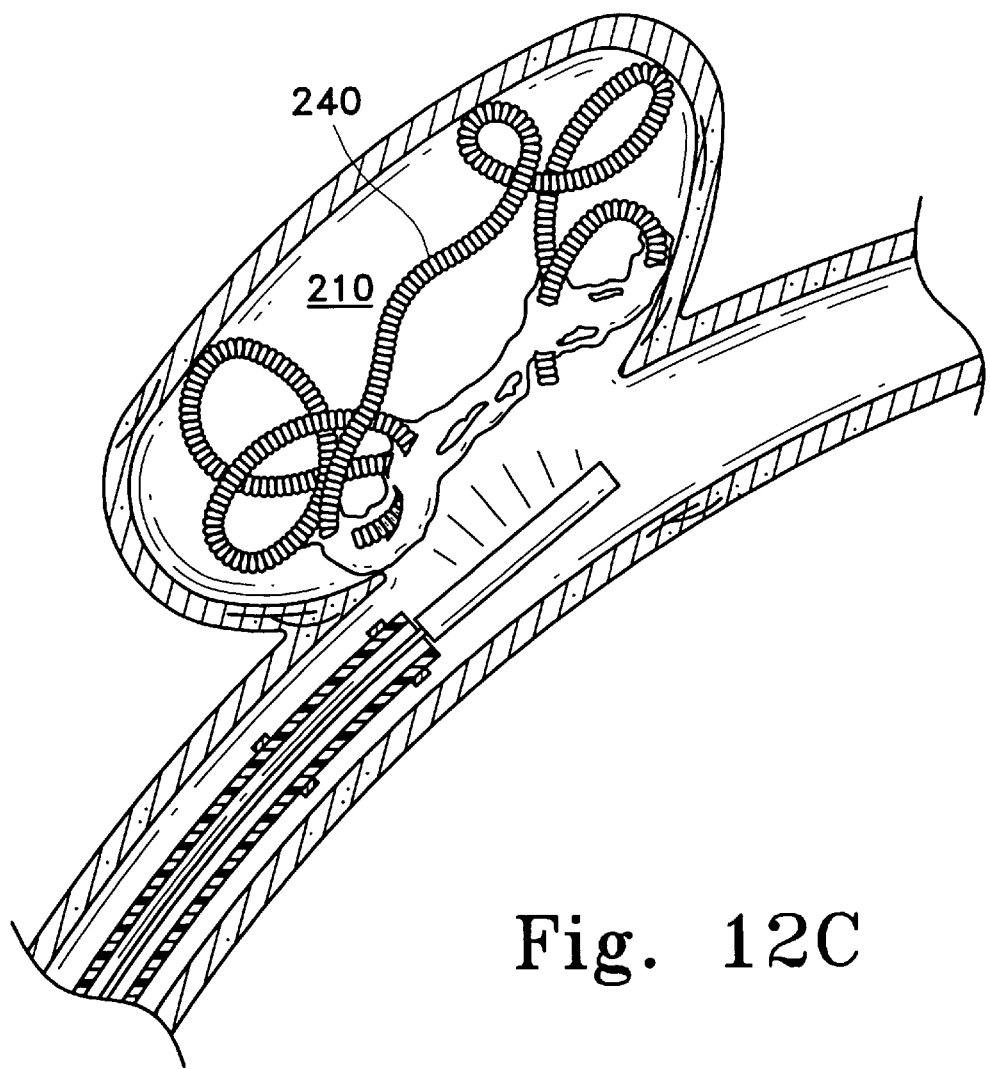

One final variation, although certainly not limiting of the procedure described herein, is the procedure found in FIGS. 12A, 12B, 12C. In this variation, FIG. 12A is the same initial step as found in FIGS. 10A and 11A. Aneurysm (200) has in is mouth (222) a guidewire (208) for direction of catheter (204) into the space (210) within aneurysm (200).

FIG. 12B shows the introduction of a vaso-occlusive device (240) which includes on its surface a coating of polymeric composition made according to this invention. In contrast to the procedures shown in the procedures associated with procedures 10A–D and 11A–D, this procedure doesn't use any ancillary or separately introduced polymeric composition. In this way the step shown in FIG. 12C simply reforms the polymeric composition found on the outside of vaso-occlusive device (240) into a somewhat looser mass which causes the various loops of the device to coalesce and adhere to each other. The devices which are introduced into the aneurysm space (210) are devices which cause occlusions in any event. Having a modest amount of permeability in the resulting as reformed device shown in FIG. 12C is not necessarily a disadvantage. With proper placement of device (240), the occlusion as initially formed lowers the pulsing upon the wall of aneurysm (200), and as the occlusion further forms, the pulsing is eliminated altogether.

This invention has been described by direct description and by specific examples of the procedure of occluding an aneurysm. It is to be understood that methods within the spirit of this invention which are equivalent nd result in procedure are considered to be within the scope of the invention as portrayed in the appended claims.

I claim as my invention:

1. A procedure for at least partially closing a mouth of an aneurysm comprising the steps of:
   a. introducing a vaso-occlusive device and a formable polymeric material into the mouth and the aneurysm
   b. reforming said polymeric material in the mouth of the aneurysm to bind said vaso-occlusive device to at least partially close the mouth of the aneurysm.

2. The procedure of claim 1 wherein the vaso-occlusive device is electrically conductive and the reforming step is accomplished by introducing an electrical current into said vaso-occlusive device.

3. The procedure of claim 1 wherein the reforming step which comprises introducing radio frequency current adjacent to the mouth of the aneurysm.

4. The procedure of claim 1 wherein the reforming step which comprises introducing light adjacent to the mouth of the aneurysm.

5. A procedure for at least partially filling an aneurysm comprising the steps of:
   a. introducing a vaso-occlusive device and a bindable material into an aneurysm;
   b. binding said bindable material in said aneurysm to bind said vaso-occlusive device to itself.

6. The procedure of claim 5 wherein the bindable material is polymeric.

7. The procedure of claim 5 wherein the bindable material binds via introduction of heat.

8. The procedure of claim 5 wherein the bindable material binds via introduction of light.

* * * * *